United States Patent [19]
Markus et al.

[11] 4,416,986
[45] * Nov. 22, 1983

[54] METHODS OF PRODUCING HBSAG

[75] Inventors: Henry Z. Markus, Wyncote; William J. McAleer, Ambler, both of Pa.

[73] Assignee: Merck & Co., Inc., Rahway, N.J.

[*] Notice: The portion of the term of this patent subsequent to Nov. 17, 1998 has been disclaimed.

[21] Appl. No.: 225,555

[22] Filed: Jan. 16, 1981

[51] Int. Cl.³ .................. C12N 5/00; C12N 5/02; C12P 21/00

[52] U.S. Cl. ................................. 435/68; 435/240; 435/241

[58] Field of Search ............... 435/68, 241, 948, 240

[56] References Cited

U.S. PATENT DOCUMENTS 3,883,393 5/1975 Knazek et al. ................. 435/240
4,220,725 9/1980 Knazek et al. ................. 435/240
4,301,250 11/1981 McAleer ........................ 435/241

OTHER PUBLICATIONS

MacNab et al., Br. J. Cancer, 34, 509–515 (1976).
Kanzek et al., Science, 178, Oct. 6, 1972, pp. 65–66.
Quarles et al., In Vitro, 16 (2): 113–118, 1980.
Rutzky et al., JNCI vol. 63, No. 4, Oct. 1979, pp. 893–902.

Primary Examiner—Esther M. Kepplinger
Attorney, Agent, or Firm—Donald J. Perrella; Hesna J. Pfeiffer

[57] ABSTRACT

Hepatitis B surface antigen (HBsAg) is produced in vitro in high titer and purity from tissue cultures of cells that shed HBsAg. The cells are grown on hollow fiber capillary units having a molecular weight cut-off of about 10,000.

7 Claims, No Drawings

METHODS OF PRODUCING HBSAG

BACKGROUND OF THE INVENTION

Hepatitis B surface antigen (HBsAG) has been shown to be effective as a vaccine against hepatitis B disease. The usual source of this and Neomycin 50 μg/ml is circulated through the capillary unit at a flow rate of 5 ml/minute. After 2 weeks at 37° C. the temperature of the incubator is reduced and maintained at 32° C. and $10^{-4}$ M caffeine is added. Cell growth is monitored by glucose utilization. Antigen samples are taken from the extracapillary space and assayed by complement fixation. The results are summarized in the following table:

| Age of Cell Culture (days) | Complement Fixation Titer |
|---|---|
| 7 | 4 |
| 14 | 16 |
| 21 | 64 |
| 28 | 512 |
| 35 | 512 |

Elimination of the fetal calf serum does not have any significant effect on titers and facilitates further purification of the HBsAG. Conventional monolayer tissue culture systems under similar conditions produced only traces of antigen.

EXAMPLE 2

Three units of capillary bundles (Vitafiber®, Amicon) one 3P10, one P30 and one 3S100 having respectively molecular weight cut-off points of 10,000; 30,000 and 100,000 are each charged with a suspension of $6.0 \times 10^6$ cells of a freshly harvested higher HBsAG yielding clone of PLC/PRF/5 cells. The units, set-up as described in Example 1, are placed in a 37° C. incubator. After 2 hours Eagle's Minimum Essential Medium (EMEM) containing 10% fetal calf serum, L-glutamine 2 mM, and Neoymcin 50 μg/ml is circulated through the capillary unit at a flow rate of 5 ml/minute. After 2 weeks at 37° C. the temperature of the incubator is reduced and maintained at 32° C. and $10^4$ M caffeine is added. Cell growth is monitored by glucose utilization. Antigen samples are taken from the extracapillary space and assayed by complement fixation. Samples from the circulating fluid are assayed by an enzyme immunoassay (AUS2YME ™, Abbott Labs). The results are summarized in the following table:

| Day | 10,000 MW | 30,000 MW | 100,000 MW |
|---|---|---|---|
| 14 | 16 | 4 | 4 |
| 21 | 64 | 64 | 8 |
| 28 | 128 | 64 | 32 |
| 33 | 256 | 64 | 16 |
| 39 | 256 | 128 | 32 |

The unit with 10,000 molecular weight cut-off point proves superior yields although glucose consumption is similar in all three units.

What is claimed is:

1. A method for preparing hepatitis B surface antigen which comprises growing cells which shed hepatitis B surface antigen in the presence of a nutrient medium on hollow fiber capillary units having a molecular weight cut-off of about 10,000.

2. A method according to claim 1 wherein the growing is effected with two sequential stages having differing temperatures, each temperature being above room temperature with the first temperature being above the second temperature.

3. A method according to claim 2 wherein the first temperature is from about 35° to about 38° C.

4. A method according to claim 2 wherein the second temperature is from about 30° C. to about 34° C.

5. A method according to claim 2 wherein the first temperature is about 37° C. and the second temperature is about 32° C.

6. A method according to claim 2 wherein caffeine is present during the second stage.

7. A method according to claim 6 wherein the caffeine is present in an amount from about 0.0001 M to about 0.0003 M.

* * * * *